United States Patent
Behar-Cohen et al.

(10) Patent No.: US 11,986,514 B2
(45) Date of Patent: May 21, 2024

(54) COMPOSITIONS FOR TREATING MACULAR EDEMA

(71) Applicants: INSERM (INSTITUT NATIONAL DE LA SANTE ET DE LA RECHERCHE MEDICALE), Paris (FR); SORBONNE UNIVERSITE, Paris (FR); UNIVERSITE DE PARIS, Paris (FR); ASSISTANCE PUBLIQUE—HOPITAUX DE PARIS, Paris (FR)

(72) Inventors: Francine Behar-Cohen, Paris (FR); Raphael Cohen, Paris (FR); Rinath Levy-Boukris, Paris (FR); Min Zhao, Paris (FR)

(73) Assignees: INSERM (INSTITUT NATIONAL DE LASANTE ET DE LA RECHERCHE MEDICALE), Paris (FR); SORBONNE UNIVERSITE, Paris (FR); UNIVERSITE DE PARIS, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 24 days.

(21) Appl. No.: 16/642,642

(22) PCT Filed: Aug. 31, 2018

(86) PCT No.: PCT/EP2018/073510
§ 371 (c)(1),
(2) Date: Feb. 27, 2020

(87) PCT Pub. No.: WO2019/043179
PCT Pub. Date: Mar. 7, 2019

(65) Prior Publication Data
US 2020/0254069 A1    Aug. 13, 2020

(30) Foreign Application Priority Data
Sep. 1, 2017 (EP) .................................. 17306133

(51) Int. Cl.
*A61K 38/38* (2006.01)
*A61K 31/573* (2006.01)
*A61K 38/01* (2006.01)
*A61K 47/36* (2006.01)
*A61P 27/02* (2006.01)

(52) U.S. Cl.
CPC ............ *A61K 38/38* (2013.01); *A61K 38/014* (2013.01); *A61K 47/36* (2013.01); *A61P 27/02* (2018.01); *A61K 31/573* (2013.01)

(58) Field of Classification Search
None
See application file for complete search history.

(56) References Cited

U.S. PATENT DOCUMENTS

2007/0088014 A1* 4/2007 Edelman ................ A61K 47/34
514/179

FOREIGN PATENT DOCUMENTS

WO    2016197005 A1    12/2016

OTHER PUBLICATIONS

Porter (Macular Edema Treatment; https://www.aao.org/eye-health/diseases/macular-edema-treatment10/22/2020).*
Wilson et al. ("How to Give Intravitreal Injections" Apr. 2013).*
Worthington Biochemical Corporation (<https://www.worthington-biochem.com/CL/cat.html accessed Apr. 11, 2022).*
The Cleveland clinic (https://my.clevelandclinic.org/health/diseases/24310-retinoschisis accessed Oct. 27, 2023).*
NIH (https://www.nei.nih.gov/learn-about-eye-health/eye-conditions-and-diseases/macular-edema#:~:text=Macular%20edema%20happens%20when%20blood,loss%20in%20people%20with%20diabetes accessed Oct. 27, 2023).*

* cited by examiner

*Primary Examiner* — Julie Ha
*Assistant Examiner* — Tara L Martinez
(74) *Attorney, Agent, or Firm* — WCF IP

(57) ABSTRACT

This invention relates to the treatment of macular edema. Macular edema is the main cause of vision loss during diabetic macular edema, wet AMD (Age Related Macular Degeneration), retinal vein occlusion and chronic intraocular inflammation. Currently, beyond photocoagulation by laser irradiation, two types of drugs are used, protein molecules that neutralize VEGF family members and glucocorticoids, with different mechanisms of action, but targeting one single symptom: macular edema. The inventors have now found that macular edema may be treated by increasing the oncotic pressure of the vitreous. According to the inventors' understanding, causing an increase in the oncotic pressure of the vitreous induces a liquid flow from the interstitial water accumulated in the retina tissue to the vitreous compartment, so as to reduce or stop macular edema. Increasing the oncotic pressure of the vitreous is preferably performed by intravitreal injection of an oncotic pressure-increasing macromolecule, which macromolecule may be selected in a group comprising protein or non-protein macromolecules, such as albumin, gelatin, alpha2 macroglobulin, fibrinogen, haptoglobin multimers, beta lipoproteins and antibodies, as well as dextran and hydroxyethyl starch.

4 Claims, 2 Drawing Sheets

COMPOSITIONS FOR TREATING MACULAR EDEMA

FIELD OF THE INVENTION

This invention relates to the field of pharmaceutical compositions for treating macular edema, which encompasses macular edema occurring in disorders or diseases selected in a group comprising wet age-related macular degeneration and other types of choroidal neovascularization, diabetic retinopathy, uveitis, retinal vein occlusion or retinal branch vein occlusion, retinis pigmentosa and pseudophakic macular edema.

BACKGROUND OF THE INVENTION

Macular edema (ME) is defined as the abnormal increase of fluid volume in the macula. Extracellular fluid can infiltrate retinal layers, and/or accumulate in cavities commonly referred to as "cysts" and/or collect in the sub-retinal space, where it is referred to as subretinal fluid (SRF). ME results from an imbalance between fluid entry and fluid exit, both mechanisms being frequently deregulated by multiple factors in retinal diseases.

Retinal edema is a consequence of an imbalance between fluid entry, fluid exit and tissue hydraulic conductance. In most retinal diseases, macular edema is multifactorial and results from multiple and intricate mechanisms, but in certain specific conditions, one single of these mechanisms predominates, allowing a better analysis of each component.

ME is a major public health problem and one of the major causes of visual impairment in the time course of many metabolic, vascular and inflammatory retinal diseases. It affects worldwide around 7 million subjects due to diabetes (Yau et al., 2012, Diabetes Care 35, 556-564. doi:10.2337/dc11-1909) and 3 million subjects due to vein occlusion (Rogers et al., 2010, International Eye Disease Consortium, 2010. The prevalence of retinal vein occlusion: pooled data from population studies from the United States, Europe, Asia, and Australia. Ophthalmology 117, 313-319.e1. doi: 10.1016/j.ophtha.2009.07.017). Forty percent of uveitic patients develop ME (Levin et al., 2014, Ophthalmology 121, 588-595.e1. doi: 10.1016/j.ophtha.2013.09.023). In industrialized countries, 5% of individuals older than 60 years of age have macular edema due to neovascular age-related macular degeneration (AMD) which causes ME (Pennington and DeAngelis, 2016, Eye Vis. 3. doi:10.1186/s40662-016-0063-5). ME is one of the major retinal causes of visual impairment but also the most accessible to treatment.

Macular edema is the main cause of vision loss during diabetic macular edema, wet AMD (Age Related Macular Degeneration), retinal vein occlusion and chronic intraocular inflammation. It occurs in the time course of almost all retinal diseases as a common mechanism of tissue response to retinal injury.

The major mechanisms leading to the inner blood-retinal barrier increased permeability are:
- Loss and/or dysfunction of cells constituting the barrier (endothelial cells, pericytes, macroglial cells),
- Alteration of the intercellular junction proteins through down-regulation or change in phosphorylation state and loss of membrane anchoring (Klaassen et al., 2013, Prog. Retin. Eye Res. 34, 19-48. doi:10.1016/j.preteyeres.2013.02.001; (Antonetti et al., 1999, J. Biol. Chem. 274, 23463-23467). and
- Deregulation of trans-endothelial transport.

The major mechanisms leading to reduced drainage mechanisms are
- Loss and/or altered function of retinal pigment epithelial cells (RPE cells)
- Loss and/or dysfunction of retinal glial Muller cells (macroglial cells)
- Alteration of proteic gradiants between vitreous, retina and choroid secondary to barriers breakdown and/or increased transcellular permeability (such as increased fenestrations in choroidal endothelial cells)

To date, all medical treatments administered into the eye for wet AMD, diabetic retinopathy, or vein occlusion target macular edema and the subsequent vision decrease.

Currently, two types of drugs are used, proteic molecules that neutralize VEGF family members and glucocorticoids, with different mechanisms of action, but targeting one single symptom: macular edema As the conventional therapy of macular edema, photocoagulation by laser irradiation, vitreous surgery and systemic administration, intravitreal administration and sub-Tenon administration of steroid have been performed. The photocoagulation by laser irradiation closes abnormal leaky blood vessel, stimulates RPE drainage mechanisms and increases Bruch membrane permeability, thus decreasing swelling of the macula. However, attention should be paid in laser irradiation to avoid extremely vulnerable fovea. Moreover, plural laser surgeries are often required to eliminate swelling. While vitreous surgery is applied to a case for which a laser surgery is ineffective, it is associated with high tissue-invasive potential, sometimes causing problems of post-surgery complications. Efficacy of laser or conventional surgery remains low and a second choice as compared to intravitreous drugs.

In addition, the administration of steroid is reported to be useful. While systemic administration of steroid is possible for the treatment of ocular diseases, in general, it often causes side effects which are too severe for ophthalmologic uses.

Although intravitreal administration can solve some drawbacks associated with systemic administration, intravitreal administration of existing ophthalmic compositions can cause ocular hypertension, steroid glaucoma and cataract when steroid is administered.

Whilst anti-VEGF drugs and steroids both efficiently reduce macular edema of various origins, there is a weak correlation between VEGF ocular levels and diabetic macular edema or wet AMD (IOVS, 2009; 50:6). Indeed, VEGF levels are mostly elevated in cases of proliferative diabetic retinopathy, when neovascularization develop at the surface of the retina (Bromberg-White J et al IOVS 2013; 54, 10:6474) (Mc Auley A K. et al. Journal of diabetes and its complications. 2014; 28:419-425). Interestingly, there is a good correlation between the macular thickness and many other cytokines in the ocular media, such as MCP1, IL1, IL6, IL8, but not VEGF (Yoshimura T et al Plos One 2009; 4:e8158—Funatsu H et al. Graefes Arch Clin Exp Ophthalmol. 2005; Sonoda S et al. Retina. 2014 April; 34(4):741-8-Oh I et al. Current Eye Research. 2010).

In all circumstances when macular edema is present, many pro-inflammatory, known to induce ocular barriers rupture are expressed and measured in ocular media, such as TNF-alpha, IL1 beta, IL6, IL8, MCP1. But anti-VEGF only neutralizes VEGF family members, whilst steroids decrease all pro-inflammatory cytokines and surprisingly both drugs have comparable efficacy, and sometimes even in the same patient.

In patients suffering from ME, intravitreous vascular endothelial growth factor (VEGF) concentrations have been shown to be increased (Fine et al. (2001) Am J Ophthalmol. 132(5):794-6, Weiss et al. (2009) Eye (Lond). 23(9):1812-8). This finding has provided a rationale for treating ME with antibodies directed against VEGF. For example, patients with ME refractory to standard treatments with anti-inflammatory drugs have been treated with some success using intravitreal bevacizumab injections (Bae et al. (2011) Retina 31(1):111-8). Combination therapy of intravitreal bevacizumab and triamcinolone has also been reported (Cervantes-Castañeda et al. (2009) Eur J Ophthalmol. 19(4):622-9).

The effects of intravitreal anti-VEGF antibodies injections are generally short-lived (Barkmeier & Akduman (2009) Ocul Immunol Inflamm. 17(2):109-17, Bae et al. (2011) Retina 31(1):111-8). Similarly, treatment of macular edema secondary to cataract surgery using intravitreal anti-VEGF therapy with anti-VEGF antibodies frequently only results in a short-term improvement of visual acuity (Buchholz et al. (2010) Dev Ophthalmol. 46:111-22).

In diabetic macular edema, only one third of the patients have an optimal response to anti-VEGF therapy (resolution of edema, and more than 15 letters of VA improvement). Anatomical response is better with 2 mg aflierceopt as compared to 0.3 mg ranibizumab. [Change in Diabetic Retinopathy Through 2 Years: Secondary Analysis of a Randomized Clinical Trial Comparing Aflibercept, Bevacizumab, and Ranibizumab. Bressler S B, Liu D, Glassman A R, Blodi B A, Castellarin A A, Jampol L M, Kaufman P L, Melia M, Singh H, Wells J A; Diabetic Retinopathy Clinical Research Network. JAMA Ophthalmol. 2017 Jun. 1; 135 (6):558-568].

The currently used intraocular anti-angiogenic agents and glucocorticoid formulations indicated in the most common retinal diseases (wet AMD, diabetic retinopathy, and vein occlusion), have been approved for their effect on ME and subsequent visual acuity gain. Such treatments are cost effective when taking into account the major impediment of macular edema on patient's life (Romero-Aroca et al., 2016, J. Diabetes Res. 2016, 2156273. doi:10.1155/2016/2156273), but represent an important burden on worldwide health care systems (Hodgson et al., 2016, Therapy. Mol. Pharm. 13, 2877-2880. doi:10.1021/acs.molpharmaceut.5b00775; Ross et al., 2016, JAMA Ophthalmol. 134, 888-896. doi:10.1001/jamaophthalmol.2016.1669).

Thus, there remains a need for treatments of macular edema that are alternative or improved as compared with the known therapy strategies. Notably, there is a need for further therapy of macular edema which shall be safe and more cost-effective than the existing therapeutic treatments.

SUMMARY OF THE INVENTION

This invention relates to an oncotic pressure-increasing macromolecule, which does not recognize VEGF as an active ingredient in a composition for its use by intravitreous injection, for treating macular edema.

In some embodiments, the said macromolecule is selected in the group of protein macromolecules and non-protein macromolecules.

In some embodiments, the protein macromolecule is selected in the group consisting of albumin and gelatin.

In some embodiments, the said composition is a 1%-25% w/w albumin aqueous composition.

In some embodiments, the said composition is a 2%-10% w/w gelatin composition.

In some embodiments, the non-protein macromolecule is selected in the group consisting of dextran and hydroxyethyl starch.

In some embodiments, the said composition is a 0.1%-15% w/w hydroxyethyl starch composition In some embodiments, the said composition is a 3%-20% w/w dextran composition In some embodiments, the said composition is adapted for dosage units having a volume ranging from 10 µl to 500 µl.

In some embodiments, the said composition is intended for treating a macular edema disorder selected in the group consisting of age-related macular degeneration, diabetic retinopathy, uveitis, retinal vein occlusion, retinoschisis, retinis pigmentosa, pseudophakic macular edema In some embodiments, the said composition further comprises an anti-inflammatory active ingredient.

In some embodiments, the said composition further comprises a mineralocorticoid receptor antagonist

DETAILED DESCRIPTION OF THE INVENTION

Figure 1:
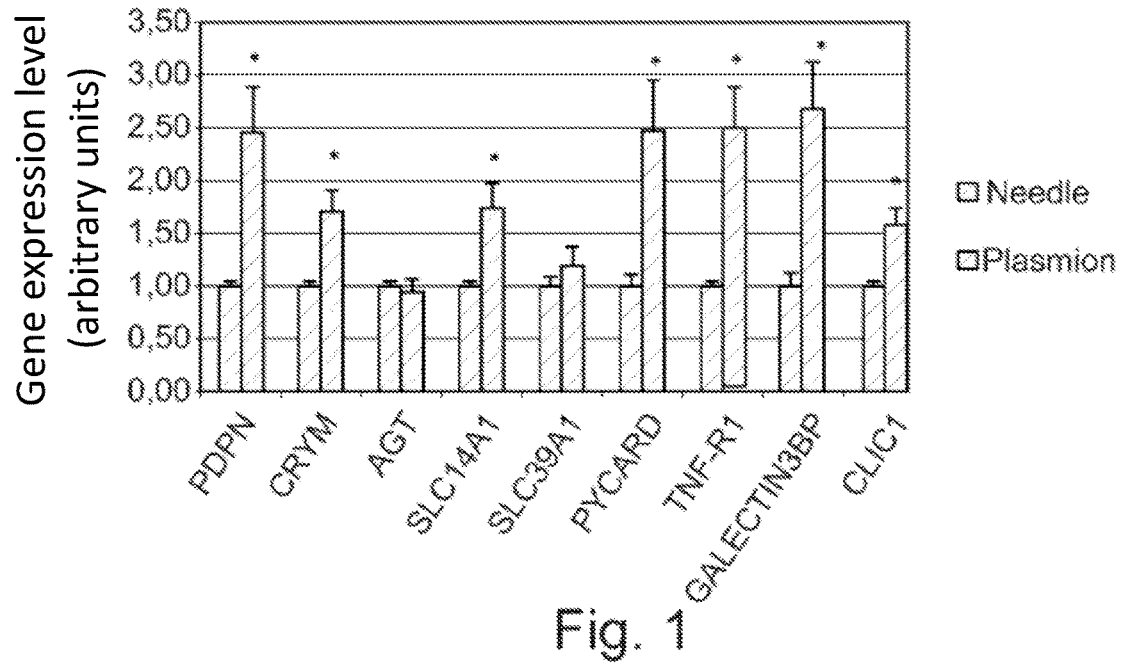
FIG. 1 illustrates the gene expression level of selected genes in the retina upon increasing vitreous oncotic pressure with a 3% w/w gelatin composition (Plasmion®). Ordinates: gene expression level, as expressed in arbitrary units. Abscissa: each group of two bars depicts the expression level of a specific selected gene with (i) left bar for control experiment and (ii) right bar for intravitreous injection of Plasmion®. Group of two bars, from the left to the right of FIG. 1 represent the following selected genes: PDPN, CRYM, AGT, SLC14A1, SLC39A1, PYCARF, TNF-R1, GALECTIN38P and CLIC1.

Unexpectedly, the present inventors have shown that macular edema may be treated by increasing the oncotic pressure in the vitreous cavity.

Without wishing to be bound by any particular theory, the inventors believe that increasing the oncotic pressure of the vitreous causes an aqueous efflux from the extracellular fluids that have infiltrated the retinal layers where proteins have accumulated to form the cysts characteristic of macular edema, the said aqueous efflux being directed towards the vitreous.

Thus, the inventors believe that causing an increase in the oncotic pressure of the vitreous induces a liquid flow from the interstitial water accumulated in the retina tissue to the vitreous compartment, so as to reduce or stop macular edema.

The present inventors have shown that macular edema may be treated by administering in the vitreous a composition that increases the oncotic pressure and more precisely a composition comprising at least one oncotic pressure-increasing macromolecule.

In some embodiments, the said oncotic pressure-increasing molecule is selected in a group of oncotic pressure-increasing macromolecules which do not recognize a cytokine, and most preferably a human cytokine, and especially oncotic pressure-increasing macromolecules which do not recognize VEGF, and most preferably oncotic pressure-increasing macromolecules which do not recognize human VEGF.

Otherwise said, in some embodiments, the oncotic pressure-increasing macromolecules that may be used according to the present invention do not encompass oncotic pressure-increasing macromolecules that recognize a cytokine, and especially do not encompass oncotic pressure-increasing macromolecules that recognize a human cytokine.

Oncotic pressure-increasing macromolecules that recognize a cytokine consist of oncotic pressure-increasing macromolecules that bind specifically to the said cytokine. In some embodiments, oncotic pressure-increasing macromolecules consist of pressure-increasing macromolecules that bind specifically to the said cytokine and neutralize its biological activity.

Thus, oncotic pressure-increasing macromolecules that recognize a cytokine encompass those which neutralize the known biological activity of the said cytokine.

Oncotic pressure-increasing macromolecules that recognize a cytokine encompass antibodies directed against the said cytokine.

As used herein, cytokines encompass those selected in a group comprising interleukins, interferons, growth factors, and TNF-related cytokines.

As used herein, the term "comprising" encompasses "consisting essentially of" and "consisting of".

Interleukins (ILs) encompass IL-1 to IL-35, which include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34 and IL-35.

Interferons encompass interferon alpha, interferon beta and interferon gamma.

Growth factors encompass TGF-alpha (Transforming Growth Factor alpha), TGF beta (Transforming Growth Factor beta), FGF (Fibroblast Growth Factor, and especially FGF-1 to FGF-23), G-CSF (Granulocyte Colony Stimulating Factor), M-CSF (Macrophage Colony Stimulating Factor), GM-CSF (Granulocyte Macrophage Colony Stimulating Factor), PLGF (Placental Growth factor), VEGF (Vascular endothelial Growth Factors), EGF (Epidermal Growth factor), GDF-9 (Growth Differenciation Factor-9), HGF (Hepatocyte Growth Factor), HDGF (Hepatoma-Derived Growth Factor), IGF-1 (Insulin Growth Factor 1), IGF-2 (Insulin Growth Factor 2) and EPO (Erhyhropoietin).

FGFs encompass FGF-1 to FGF-23, which include FGF-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22 and FGF-23.

TNF-related cytokines encompass TNF-alpha (Tumor Necrosis Factor alpha), TNF-beta (Tumor Necrosis Factor beta), LT alpha (Lymphotoxin alpha), LT beta (Lymphotoxin beta).

Thus, in some embodiments, this invention relates to an oncotic pressure-increasing macromolecule which does not recognize VEGF, as an active ingredient in a composition for its use by intravitreous injection, for treating macular edema.

Without wishing to be bound by any particular theory, the inventors believe that increasing the oncotic pressure within the vitreous cavity not solely passively induces an aqueous efflux from the retina layer but also activates the expression of various proteins, including a plurality of protein pumps, that may contribute to the aqueous liquid transfer from the retina cysts towards the vitreous compartment, as it is illustrated by the gene activation that has been observed.

More precisely, the inventors have shown that increasing the oncotic pressure of the vitreous induces an up-regulation of a plurality of genes involved in fluxes exchanges in the retina, such as Clic1, Pdpn (encoding podoplanin), Pycard, Serpin A3 (encoding alpha 1 antichymotrypsin), Slc14a1 (encoding an urea and water transporter), Spp1 (encoding osteopontin), Timp1 (metalloprotease inhibitor 1) and Lcn2 (lipocalin-2 or Ngal, which regulates the activity of MMP9). Noticeably, (i) Clic proteins are involved in the maintenance of microvillar structures, phagocytosis and vesicle trafficking, (ii) Pdpn is involved in lymphangiogenesis, which is associated with protein drainage and diseases associated with PDPN include Lymphangioma, (iii) Lack of a functional Serpin A3 results in early-onset panlobular emphysema, (iv) Slc14a1 protein transports both urea and water and is endowed with a relatively high transport rate. The rate of urea conduction is increased by hypotonic stress since urea is a osmoregulator (v) In the retina, osteopontin encoded by Spp1 is released from retinal glial (Müller) cells and inhibits the swelling of rat Müller cells induced by hypoosmotic exposure, (vi) TIMP1/MMP9 is an important regulator of blood-brain barrier and TIMP1 induces occlusion expression through inhibition of MMP2 and (vii) Lcn2 regulates the activity of MMP9 and possesses multiple roles in permeability. Interestingly, TIMP-1/MMP-9 Imbalance is involved in experimental in brain edema in rats.

Thus, it is shown in the examples herein that increasing the oncotic pressure in the vitreous compartment by injection therein of a macromolecule allows treating macular edema, although the exact underlying mechanisms of the observed retinal efflux are not precisely known.

As shown in the examples herein, the same edema reduction effect is reached, irrespective of whether the oncotic pressure-increasing macromolecule consists or not of a molecule known as a cytokine inhibitor, and especially irrespective of whether the oncotic pressure-increasing macromolecule consists or not of a molecule known as a VEGF inhibitor.

Notably, the inventors have shown that almost the same effect on the upregulation of gene expression is obtained by an intravitreous injection of (i) a therapeutic anti-VEGF antibody Fab fragment such as ranibizumab and (ii) an unrelated polyclonal Fab fragment (89% of differentially expressed genes in common).

Further, the inventors have shown that almost the same effect on the regulation of gene expression is obtained by an intravitreous injection of (i) a therapeutic anti-VEGF antibody such as bevazucimab and (ii) an unrelated isotypic human IgG.

Unexpectedly and highly importantly, it has been shown herein that the same effect of edema reduction is obtained by an intravitreous injection of (i) a therapeutic anti-VEGF antibody such as bevazucimab, (ii) an unrelated Fab fragment and (iii) an oncotic pressure-increasing macromolecule which does not recognize a cytokine, in particular which does not recognize VEGF, such as a 3% w/w gelatin composition.

A surprising inventors' finding is that anti-VEGF, injected repeatedly in the vitreous of patients with wet AMD and choroidal neovascularization do not suppress the neovessels, thus requiring multiple and repeated injection to reduce macular edema.

Another surprising finding is that ranibizumab (therapeutic anti-VEGF Fab fragment) nor bevacizumab (therapeutic anti-VEGF antibody) do not neutralize murine VEGF (Patel J L et al Exp Eye Res 2006; 798-806), although a high number of publications describe the effects of these active ingredients on various murine models of neovascularization, tumors, etc.

The unexpected inventors' experimental results depicted in the examples herein have led them to reconsider the scientific literature related to the treatment of macular edema with anti-VEGF active ingredients.

Importantly, whilst therapeutic anti-VEGF molecules have been optimized for increased binding affinity to VEGF and whilst the $IC_{50}$ for vessel proliferation induced by VEGF is of 100 pM for ranibizumab and aflibercept (a fusion protein comprising VEGF receptor domains fused to an antibody Fc), the minimal concentration of ranibizumab in the vitreous required to maintain the retina dry is 10 µM. The dose of aflibercept injected in the vitreous every 8 weeks is of 2 mg, the monthly injected dose of ranibizumab is of 0.5 mg and the monthly injected dose of bevacizumab is of 1.25 mg. Moreover, the clinical studies did not show any dose response for these different active ingredients. There is thus a discrepancy between (i) the very high potency of these biologic molecules to neutralize the biological activity of VEGF and (ii) the high doses required to get clinical efficacy since VEGF levels in the human eyes with diabetic retinopathy remain as low as 5-10 ng/ml and there are nor increased in eyes with macular edema (ME) due to wet age-related macular degeneration (AMD).

At least part of the above literature's confusing results have found a rationale in the examples herein, which is that the high dose ranges of anti-VEGF molecules that are injected within the vitreous compartment cause an increase in the vitreous oncotic pressure, which vitreous oncotic pressure increase induced the aqueous efflux from the edemic retina tissue cysts, thus leading to a reduction of the macular edema.

Altogether, the inventors' findings have led to conceive a method for treating macular edema based on a strategy of increasing the oncotic pressure of the vitreous, so as to induce an aqueous flow from the retina's cysts and retina interstitial tissues, possibly towards the vitreous. The aqueous efflux allows emptying the retina's cysts and thus allows reducing or resorbing macular edema.

This invention relates to an oncotic pressure-increasing macromolecule which does not recognize a cytokine, as an active ingredient in a composition for its use by intravitreous injection for treating macular edema in a human individual.

In preferred embodiments, the invention relates to an oncotic pressure-increasing macromolecule which does not recognize a cytokine, as an active ingredient in a composition for its use by intravitreous injection for treating macular edema.

Notably, this invention relates to an oncotic pressure-increasing macromolecule, which does not recognize VEGF as an active ingredient in a composition for its use by intravitreous injection for treating macular edema.

This invention also concerns the use of an oncotic pressure-increasing macromolecule which does not recognize a cytokine as an active ingredient for preparing a medicament adapted to intravitreous injection for treating macular edema.

Notably, this invention also concerns the use of an oncotic pressure-increasing macromolecule which does not recognize VEGF as an active ingredient for preparing a medicament adapted to intravitreous injection for treating macular edema.

This invention also pertains to a method for treating macular edema comprising a step of administering by intravitreous injection, to an individual in need thereof, an oncotic pressure-increasing macromolecule which does not recognize a cytokine.

Notably, this invention also pertains to a method for treating macular edema comprising a step of administering by intravitreous injection, to an individual in need thereof, an oncotic pressure-increasing macromolecule which does not recognize VEGF.

The term "oncotic pressure" is used herein in its conventional meaning admitted in the art, which is also termed "colloidal osmotic pressure" in the art. As a reminder, oncotic pressure is a form of osmotic pressure exerted by proteins, notably albumin, in a blood vessel's plasma (blood/liquid) that usually tends to pull water into the circulatory system. It is the opposing force to hydrostatic pressure. Oncotic pressure is the part of osmotic pressure which is contributed by the large molecules, the "colloid osmotic pressure" (also termed "COP").

It is herein reminded that colloids is a term used to collectively refer to the large molecular weight (nominally MW>30,000) particles present in a solution. In normal plasma, the plasma proteins are the major colloids present. As the colloids are solutes they contribute to the total osmotic pressure of the solution. This component due to the colloids is typically quite a small percent of the total osmotic pressure. It is referred to as colloid osmotic pressure (or sometimes as the oncotic pressure). In plasma, the oncotic pressure is only about 0.5% of the total osmotic pressure. This may be a small percent but because colloids cannot cross the capillary membrane easily, oncotic pressure is extremely important in transcapillary fluid dynamics. Osmotic pressure contribution of albumin to colloidal interactions is described in Mukta Singh-Zocchi,*†‡ Anita Andreasen,* and Giovanni Zocchi* Proc Natl Acad Sci USA. 1999 Jun. 8; 96(12): 6711-6715. It is generally admitted that albumin contributes 75% to the oncotic pressure of the plasma in mammals, and especially in human. Measurement of the oncotic pressure of a macromolecule-containing solution may be performed by methods known in the art, such as those described by Morissette (1977, CMA Journal, Vol. 116: 897-900), Barclay et al. (1987, Intensive care medicine, Vol. 13 (n° 2): 114-118) and by Miller et al. (1988, Kidney International, Vol. 34: 220-223). The oncotic pressure of a macromolecule-containing solution may notably be measured by using a measurement device such as disclosed in the U.S. Pat. No. 2,716,886 or such as disclosed by Bisera et al. (1978, Clin Chem, Vol. 24 (n° 9): 1586-1589). It is admitted in the art that, in an ideal condition (i.e. in a rather non-complex medium such as the vitreous medium), the oncotic pressure value is given by the Van't Hoff's formula (1) below (1985, Van Holde, Physical Chemistry, 2nd Ed. Englewood Cliffs, NJ:Prentice Hall):

$$COP = R \times T \times C \quad (1), \text{ wherein:}$$

COP is the oncotic pressure value (or Colloid osmotic pressure value), e.g. as expressed in mm Hg,
C is the molar colloid concentration, e.g. as expressed in g/L,
R is the universal gas constant, e.g. as expressed in litre×atm K$^{-1}$ mol$^{-1}$, and
T is the absolute temperature An oncotic pressure value of a liquid solution may be expressed as mm Hg or also as Pa, it being reminded that there is the following relationship: 1 mm Hg=133.322 Pa.

The present inventors have determined that an increase of the vitreous oncotic pressure allowing treatment of macular edema, irrespective of the resulting absolute value of the resulting increased vitreous oncotic pressure, is reached by administering within the vitreous a macromolecule-containing composition.

As it is known in the art, the oncotic pressure of a liquid solution does not rely upon the weight of the macromolecules but instead relies upon the number of dissolved molecules, which explains why the oncotic pressure of a macromolecule-containing liquid solution relies on the number average molecular weight ("Mn") of the population of macromolecules contained therein.

As used herein, the term "number average molecular weight" or "Mn" is used in its conventional meaning admitted in the art, which is the statistical average molecular weight of all the polymer chains in the sample, and is defined by: formula (1) below:

$$Mn = \Sigma NiMi / \Sigma Ni \quad (1), \text{ wherein:}$$

Mi is the molecular weight of a chain, and
Ni is the number of chains of that molecular weight.

Mn can be predicted by polymerization mechanisms and, for some polymeric macromolecules, is measured, by methods that determine the number of molecules in a sample of a given weight; for example, colligative methods such as end-group assay. If Mn is quoted for a molecular weight distribution, there are equal numbers of molecules on either side of Mn in the distribution.

It shall be understood that although the strategy for treating macular edema described in the present specification is based on the showing that inducing an increase of the oncotic pressure in the vitreous allows reducing or resorbing the cysts located in the retinal tissue and the interstitial fluid, the oncotic pressure value is not by itself an important parameter, since the inventors have shown that a desired increase in oncotic pressure is reached by macromolecules having a minimal number average molecular weight.

In some embodiments, the macromolecule-containing composition behaves as a monodisperse liquid solution, especially when all the macromolecules contained therein are of the same molecular weight, thus especially when the said macromolecule consists of a protein.

In some other embodiments, the macromolecule-containing composition behaves as a polydisperse liquid solution, especially when the said composition comprises a population of macromolecules having distinct molecular weight, such as for compositions comprising hydroxyethyl starch, gelatin or dextran as the oncotic pressure-increasing macromolecule. For a macromolecule population generating polydisperse liquid solution, the number average molecular weight (Mn) is currently of the same order of magnitude as the mean molecular weight (Mw). Illustratively, most if not all commercialized dextrans have an extremely low polydispersity, with Mw/Mn ratio values close to 1.0.

Consequently, the inventors have shown herein that a desired increase in oncotic pressure of the vitreous for treating macular edema is preferably obtained by intravitreous injection of macromolecules having a minimal mean molecular weight (Mw, also termed "Molecular weight" herein), and more precisely by injection of macromolecules having a molecular weight (Mw) of 30 kDa or more.

Further, the inventors have determined that an efficient macular edema reduction is reached with a macromolecule-containing composition wherein the said macromolecule has a molecular weight of 30 kDa or more.

In preferred embodiments, an efficient macular edema reduction is reached with a macromolecule-containing composition wherein the said macromolecule has a molecular weight ranging from 25 kDa and 300 KDa, such as a molecular weight ranging from 25 kDa to 200 kDa, which includes a molecular weight ranging from 25 kDa to 160 kDa.

As used herein, a "macromolecule" consists of a polymeric molecule composed of one or more chains, each chain comprising a plurality of units which are linked one to another and wherein the said macromolecule has a molecular weight of 25 kDa or more.

According to the invention, there is no precise upper limit to the molecular weight of the macromolecule which is used, provided that (i) the said macromolecule remains in suspension both (a) in a ready-to-use composition to be administered and (b) in the vitreous, once the composition has been injected, and provided that (ii) the injected composition induces a resorption of the treated macular edema.

However, it is believed that macromolecules having a molecular weight of more than 300 kDa might not be appropriate, since the viscosity of the resulting macromolecule-containing composition may be to much high for a convenient administration. Further, it is believed that macromolecules having a molecular weight of more than 300 kDa may have a propensity to aggregate, which is inappropriate for a medical use.

Thus, the present invention relates to an oncotic pressure-increasing macromolecule having a molecular weight of 25 kDa or more which does not recognize a cytokine, and especially which does not recognize VEGF, as an active ingredient in a composition for its use by intravitreous injection for treating macular edema.

This invention also concerns the use of an oncotic pressure-increasing macromolecule having a molecular weight of 25 kDa or more which does not recognize a cytokine, and especially which does not recognize VEGF, as an active ingredient for preparing a medicament adapted to intravitreous injection for treating macular edema.

This invention also pertains to a method for treating macular edema comprising a step of administering by intravitreous injection, to an individual in need thereof, an oncotic pressure-increasing macromolecule having a molecular weight of 25 kDa or more which does not recognize a cytokine, and especially which does not recognize VEGF.

The present invention relates to an oncotic pressure-increasing polymeric molecule having a molecular weight of 25 kDa or more which does not recognize a cytokine, and especially which does not recognize VEGF, as an active ingredient in a composition for its use by intravitreous injection for treating macular edema.

This invention also concerns the use of an oncotic pressure-increasing polymeric molecule having a molecular weight of 25 kDa or more which does not recognize a cytokine, and especially which does not recognize VEGF, as an active ingredient for preparing a medicament adapted to intravitreous injection for treating macular edema.

This invention also pertains to a method for treating macular edema comprising a step of administering by intravitreous injection, to an individual in need thereof, an oncotic pressure-increasing polymeric molecule having a molecular weight of 25 kDa or more which does not recognize a cytokine, and especially which does not recognize VEGF.

The present invention relates to a macromolecule having a molecular weight of 25 kDa or more which does not recognize a cytokine, and especially which does not recognize VEGF, as an active ingredient in a composition for its use by intravitreous injection for treating macular edema.

This invention also concerns the use of a macromolecule having a molecular weight of 25 kDa or more, which does not recognize a cytokine, and especially which does not recognize VEGF, as an active ingredient for preparing a medicament adapted to intravitreous injection for treating macular edema.

This invention also pertains to a method for treating macular edema comprising a step of administering by intravitreous injection, to an individual in need thereof, a macromolecule having a molecular weight of 25 kDa or more which does not recognize a cytokine, and especially which does not recognize VEGF.

The present invention relates to a polymeric molecule having a molecular weight of 25 kDa or more which does not recognize a cytokine, and especially which does not recognize VEGF, as an active ingredient in a composition for its use by intravitreous injection for treating macular edema.

This invention also concerns the use of a polymeric molecule having a molecular weight of 25 kDa or more which does not recognize a cytokine, and especially which does not recognize VEGF, as an active ingredient for preparing a medicament adapted to intravitreous injection for treating macular edema.

This invention also pertains to a method for treating macular edema comprising a step of administering by intravitreous injection, to an individual in need thereof, a polymeric molecule having a molecular weight of 25 kDa or more which does not recognize a cytokine, and especially which does not recognize VEGF.

In some embodiments, an oncotic pressure-increasing macromolecule is a protein having a molecular weight of 25 kDa or more. Because most proteins are composed of a unique polymeric amino acid chain, their number average molecular weight (Mn) equals their weight average molecular weight (Mw), which is also their conventionally used molecular weight value.

As used herein, a macromolecule, or a polymeric molecule, "which does not recognize a cytokine" consists of a macromolecule, or a polymeric molecule, which has not the ability of specifically binding to the said cytokine, even if the said macromolecule (or polymeric molecule) may occasionally non-specifically bind to the said cytokine, especially may non-specifically bind to the said cytokine with a low affinity.

As used herein, a macromolecule, or a polymeric molecule, "which does not recognize VEGF" consists of a macromolecule, or a polymeric molecule, which has not the ability of specifically binding to VEGF, even if the said macromolecule (or polymeric molecule) may occasionally non-specifically bind to VEGF, especially may non-specifically bind to VEGF with a low affinity.

Illustratively, antibodies directed against a cytokine or cytokine fragments or variants thereof, as well as cytokine-binding antibody fragments or variants, are expressly excluded as being encompassed by the macromolecules, or the polymeric molecules, that may be used for increasing oncotic pressure according to the present invention.

Illustratively, antibodies directed against VEGF, as well as VEGF-binding antibody fragments or variants thereof, are expressly excluded as being encompassed by the macromolecules, or the polymeric molecules, that may be used for increasing oncotic pressure according to the present invention.

Further illustratively, other molecules binding to a cytokine such as cytokine receptors, as well as cytokine-binding fragments or variants thereof, are also expressly excluded as being encompassed by the macromolecules, or polymeric molecules, that may be used for increasing oncotic pressure according to the present invention.

Still illustratively, other molecules binding to VEGF such as VEGF receptors, as well as VEGF-binding fragments or variants thereof, are also expressly excluded as being encompassed by the macromolecules, or polymeric molecules, that may be used for increasing oncotic pressure according to the present invention. Variants of VEGF receptors encompass VEGF-binding domains of VEGF receptors that may be fused to a Fc fragment of an immunoglobulin.

As used herein, VEGF encompasses any mammal Vascular Endothelial Growth Factor, and especially human Vascular Endothelial Growth Factor.

As used herein, an oncotic pressure-increasing macromolecule, or polymeric molecule, is intended to consist of an "active ingredient", which means that the said oncotic pressure-increasing macromolecule, or polymeric molecule, exerts an anti-macular edema by itself, when used alone or as combined with one or more other oncotic pressure-increasing macromolecule.

Throughout intensive research, the present inventors have determined that, it being taken into account that only small volumes shall be used for intravitreous injection, the injected macromolecule(s) shall possess a minimal oncotic-increasing capacity so as to sufficiently increase the oncotic pressure when injected within the vitreous compartment. As already specified previously, the inventors have then determined that only macromolecules having a molecular weight (Mn) of 30 kDa or more may behave as active ingredients in an anti-macular edema composition for intravitreous injection according to the invention.

Oncotic Pressure-Increasing Macromolecules

In some embodiments, the said oncotic pressure-increasing macromolecule consists of a protein macromolecule. Protein macromolecules encompass albumin, gelatin, alpha2 macroglobulin, fibrinogen, haptoglobin multimers, beta lipoproteins, antibodies or antibodies fragments that do not bind to a human protein.

In some other embodiments, the said oncotic pressure-increasing macromolecule consists of a non-protein macromolecule, such as a glycosidic macromolecule.

An oncotic pressure-increasing macromolecule as described herein encompasses notably certain macromolecules that are used in volume expansion compositions (also termed "volume expanders"), and in particular some colloid-forming macromolecules that are contained in volume expansion compositions.

Oncotic pressure-increasing macromolecules thus encompass proteins such as albumin and gelatin, as well as other colloid-forming macromolecules such as dextrans and hydroxyethyl starch (also termed "HES"), carboxymethyl-celluloses, as well as medical grade polystyrene resins.

Medical grade polystyrene resins encompass, for example, sodium polystyrene sulfonate such as that which is marketed under the brand name Kayexalate® by the company Sanofi, dextran polystyrene diblock copolymers.

Albumin

Albumin that may be used in an oncotic pressure-increasing composition described herein encompasses any available albumin, including a mammal serum albumin such as calf serum albumin, horse serum albumin and human serum albumin. In some embodiments, the said albumin is obtained by extraction and purification from natural sources such as plasma. In some other embodiments, the said albumin consists of a recombinant albumin, such as recombinant human albumin.

Human albumin is a protein composed of a simple chain of amino acids with a quaternary helix-like structure. The center of the molecule is made up of hydrophobic radicals which are binding sites for many ligands. The outer part of the molecule is composed of hydrophilic radicals. Albumin is a relatively small molecule in terms of space, but its size is sufficient to prevent it from crossing the capillary membrane. At physiological concentrations (40-45 g/L), albumin accounts for 70% of plasmas oncotic pressure, or about 18 to 22 mm Hg of which 5 to 9 mm Hg are related to the Donnan effect (the molecules electrically neutral charge).

Albumin may be extracted only from plasma collected by phlebotomy. Albumin may also be obtained from transgenic animals. Most techniques currently used are based on the Cohn principle and involve sequential fractionation of plasma proteins. Available concentrated preparations of 4% w/w, 5% w/w, 20% w/w or 25% w/w albumin solutions are under a sterile form.

Albumins that may be used in an oncotic pressure-increasing composition described herein include recombinant albumins, such as a human recombinant albumin. Illustratively, human albumin is a protein having 575 amino acid residues in length and having a molecular weight, which equals the number average molecular weight, of 69 kDa.

Dextrans

Of all the colloids used in clinical practice, dextrans are those with which medical practicioners have the most experience. The physical, chemical and pharmacological properties of dextrans are particularly well known and among the most studied of all plasma substitutes.

As a reminder, dextran is a single-chain polysaccharide of bacterial origin. The average molecular weight of these of variably dispersed solutions is an important product characteristic. The main types of dextran solutions are designated according to their Mw: 70,000 Da (dextran 70), 60,000 Da (dextran 60) and 40,000 Da (dextran 40).

Dextran 70 and 60 are generally prepared as 6% solutions, while dextran 40 is available in a 10% concentration. The colloid oncotic power of the various dextran solutions is very high.

Dextrans are complex branched glucan (polysaccharide made of many glucose units) composed of chains of varying lengths (from 3 to 2000 kDa). Dextrans are polymeric molecules of bacterial origin. Dextrans are well-known in the art, especially for their use in various medical applications, which includes their use in volume expander liquid solutions. Typically, "Dextran 40" consists of a composition comprising a population of dextran molecules having a number average molecular weight of 40 kDa and is thus encompassed as a macromolecule of interest, or polymeric molecule of interest, according to the invention. Dextran compositions of interest encompass dextran 40, Dextran 60 and Dextran 80. Dextrans that may be used according to the present invention encompass those which are marketed under the brand names of Hemodex®, Macrodex®, Rheomacrodex®, as well as Plasmacair®.

Hydroxyethyl Starches

Hydroxyethyl starches are modified natural polysaccharides. Hydroxyethyl starches (HES) may be obtained by extraction from plants, and especially from maize. As it is known in the art, starch modification by replacing, at least partly, glucose hydroxyl groups by hydroxyethyl-ether groups allows reducing starch sensitivity to enzyme hydrolysis and stabilize the resulting modified starch molecules in liquid solution. Hydroxylation or etherification are used to stabilize the solution and slow, and increase the molecules hydrophilia considerably and expand its conformation. The extent of hydroxyethylation may be measured by two features: (i) the degree of substitution and (ii) the molar substitution ratio. This second characteristic takes into account the di- and tri-substitutions that occur with some molecules of glucose and better reflects the starchs resistance to hydrolysis by α-amylase. The site of hydoxyethylation on the glucose molecule is preferentially C2, but etherification at C3 or C6 is also possible. Hydroxyethylation at C2 gives the most resistance to α-amylase. The ratio of C2/C6 reflects the types of hydroxyethylation.

The first hydroxyethyl starch was marketed in Germany and the United States and had a high Mw (450 kDa). However, this starch had side effects on hemostasis that led to its being withdrawn from the market. Other starches with a lower molecular weight have now been developed. In France, the main products are Elohes®, Lomol®, Heafusine® and Hesteril®. These products have similar although differing characteristics. Elohes® is a 6% solution, has a Mw of 200 kD and a molar substitution rate of 0.62. Lomol® is a 10% solution, has a Mw of 250 kD and a molar substitution rate of 0.45. Hesteril® and Heafusine® have similar although not identical characteristics to Lomol® and are 6% solutions.

A classification of hydroxyethyl starches by in vitro Mw, i.e. high Mw (450 kD), medium Mw (200 kD) and low Mw (70 kD) does not take into consideration the degree of hydroxyethyl substitution or the C2/C6 ratio. The in vivo Mw depends on (i) the original Mw, (ii) the extent of hydroxyethylation and (iii) the C2/C6 ratio. The higher the values for all three of these characteristics, the higher the in vivo Mw.

Illustratively, for two distinct hydroxyethyl starches, one of which has an in vivo Mw that is half that of the others, this means that for the same concentration, the solution with the smaller Mw has twice the colloid osmotic power of the other. In other words, for the solution with the smaller Mw, half of the concentration would suffice to produce an equivalent effect.

In some embodiments, a selected hydroxyethyl starch is the one having the lowest in vivo Mw above the threshold of renal eliminiation, which is 50-60 kD. The in vivo Mw of Elohes® is 140-150 kD, higher than that of Hesteril®, at 110-120 kD.

Hydroxyethyl starches that may be used according to the present invention encompass those which are presently marketed under the brand names of Voluven®, Restorvol®, Lomol®, Heafusine®, Heloes®, as well as Hesteril®. Hydroxyethyl starches comprised in the solutions marketed under the brand names of Lomol®, Heafusine®, Heloes® and Hesteril® consist of high molecular weight HES having 200 kDa or more. Hydroxyethyl starches comprised in the solutions marketed under the brand names of Voluven® and Restorvol® consist of low molecular weight HES having about 130 kDa.

Gelatins

Gelatins became available for clinical use since the 1950s, including the current products, modified fluid gelatins and urea-bridge gelatins.

Gelatins are generally a product of bovine origin. Three factors combine to contribute to the safety of gelatins used in pharmaceuticals: (i) manufacturers must not use raw material from the United Kingdom; (ii) the tissues used as raw material are classified as not having any detectable level of infectiousness and. (iii) the method of preparation which includes extended acid and alcaline processing and filtration is sufficient to eliminate any risk.

Gelatins consist of polypeptides which are generally obtained from plant or animal collagens. In some embodiments, gelatins that may be used according to the present invention consists of gelatins of bovine origin. Gelatins contain a plurality of polymeric chains of form 8 kDa to 15 kDa. In certain types of gelatins, the constitutive polymeric chains are linked, one with another, through di-isocyanate bridges. Certain modified fluid gelatins possess polymeric chains bearing amine groups at their ends which are blocked through succinylation. The average molecular weight of gelatins is of about 35 kDa. Gelatins that may be used according to the present invention encompass those which are marketed under the brand names of Gelofusine®, Plasmion®, Plasmagel®, Geloplasma®, Hextend®, Hetastarch®, Pentastarch®, Voluven®, as well as Haemaccel®.

Pharmaceutical Compositions

Pharmaceutical compositions comprising oncotic pressure-increasing macromolecules as the active ingredients are further described herein.

Pharmaceutical compositions for their use according to the invention may be in various forms, notably in various storage forms, that is either in liquid or in solid form.

In embodiments wherein the pharmaceutical composition is in a storage liquid form, it may be used either as such or it may be diluted before use, so as to prepare a ready-to-use composition that may be subsequently injected within the vitreous.

In preferred embodiments, pharmaceutical compositions in liquid form consist of aqueous liquid solutions that may also contain a small concentration of salt (e.g. NaCl or BaCl) so as to be at an appropriate osmolarity for injection in the vitreous. In preferred embodiments, an appropriate osmolarity of the liquid solution shall not be below 290, mOsm/kg. In preferred embodiments, an appropriate osmolarity of the liquid solution shall not be not higher than 300 mOsm/kg.

In the embodiments wherein the pharmaceutical composition is under a solid form, the said composition may be in a lyophilized form or in a non-lyophilized powder form. In both forms, the preparation of the ready-to-use pharmaceutical composition requires performing a step of reconstitution by adding water or a saline aqueous solution, so as to obtain a pharmaceutical composition having the desired properties described in the present specification for treating macular edema.

According to the present invention, disorders involving a macular edema encompasses those disorders selected in a group comprising choroidal neovascularization complicating age-related macular degeneration, chronic choroidopathy including diffuse retinal epitheliopathy, inflammatory neovascularization, diabetic retinopathy, uveitis, retinal vein occlusion or branch vein occlusion, retinis pigmentosa, other retinal degeneration and pseudophakic macular edema.

As it is readily understood by the one skilled in the art, the increase of the vitreous oncotic pressure depends on (i) the macromolecule which is used as the active ingredient, on (ii) the final concentration of the said macromolecule in the pharmaceutical composition, and on (iii) the injected volume of the said composition within the vitreous compartment (i.e. on the final concentration of the said macromolecule in the vitreous compartment after administration).

For objective physiological reasons, the injected volume of a pharmaceutical composition described herein within the vitreous compartment may range from 10 µl to 500 µl, and advantageously ranges from 50 µl to 200 µl.

The final ready-to-use pharmaceutical composition consists of a liquid solution comprising one or more oncotic pressure-increasing macromolecules of interest described in the present specification.

The appropriate weight concentration of the selected macromolecule in a pharmaceutical composition for use according to the invention is easily determined by the one skilled in the art who will take benefit from guidance provided in the specification, possibly combined with his technical knowledge.

Further, for determining an optimal weight concentration of the selected macromolecule in a pharmaceutical composition as described herein, the one skilled in the art may perform the methods disclosed in the examples herein and especially may perform the described in vitro method which makes use of retinal explants. Thus, for determining in all cases the optimal concentration of the selected macromolecule for preparing a pharmaceutical composition for use according to the invention, the one skilled in the art may perform an in vitro method comprising the steps of:

a) providing a retinal explant,
b) generating a retinal edema, such as by incubating the said retinal explant in hypo-osmotic conditions during an appropriate time period,
c) performing a washing step on the explant obtained at the end of step b), and then incubating the resulting retinal explants with a candidate composition comprising a known concentration of a selected macromolecule, and
d) selecting the said candidate composition when the said composition causes a reduction of the edema in the said retinal explant.

In some embodiments, the retinal explant which is used at step a) of the method may be previously obtained by dissecting fresh enucleated rat eyes and then separate the neuroretina, which is subsequently maintained in organoculture on a paper filter in culture medium, according to a technique which is well known in the art.

The retinal implant provided at step a) encompasses a human mammal retinal explant and a non-human mammal retinal explant, such as a rat retinal explant.

At step b), hypo-osmotic conditions may be reached by using a conventional physiological saline solution to which water is added, such as to which a water volume of 40% the initial volume of the said physiological saline solution is added. The duration of the incubation step b) may vary depending on the hypo-osmotic conditions which are applied. Illustratively, step b) may be performed in a time period ranging from 1 minutes to 10 minutes, such as ranging from 3 minutes to 5 minutes, such as for example 4 minutes.

Step d) may itself comprises the following sub-steps:
d1) measuring a thickness value of the retinal explant, and
d2) comparing the thickness value measured at step d1) with a reference retinal thickness value.

In some embodiments, step d1) may be performed on one, or preferably more than one, stained cryogenized tissue section samples prepared from the retinal explant obtained at the end of step c), generally by using a microscope.

In some embodiments of step d2), the reference retinal thickness value is a retinal thickness value obtained from a retinal explant obtained at the end of step b) of the in vitro method.

As it is previously mentioned elsewhere in the present specification, pharmaceutical compositions that may be used according to the invention encompass known compositions that are presently used as volume expansion solutions, especially for managing situations of acute bleeding.

Illustratively, in embodiments wherein albumin is the macromolecule of interest, it may be used a liquid solution comprising an albumin concentration ranging from 1% w/w to 25% w/w.

The one skilled in the art may use a human albumin-containing liquid solution selected in a group comprising the compositions marketed under the brand names of Albuked®, Albumarc®, Albumin-Alpine®, Albuminar-25®, Albunex®, Alburx®, Albutein®, Buminate®, Flexbumin®, Human Albumin Grifols®, Kedbumin®, Plasbumin-25®, Plasbumin-5® and Recombunin®

Illustratively, a 4% w/w human albumin solution has an oncotic pressure of 20 to 29 mm Hg; a 25% w/w human albumin solution has an oncotic pressure of 100-120 mm Hg (Miltra et al., 2009, Indian J Anaesth, Vol. 53 (n° 5): 592-607).

In embodiments wherein the macromolecule of interest consists of a dextran, dextrans of various molecular weight may be employed, which encompass Dextran 40, Dextran 60, Dextran 70 and Dextran 80.

The dextran concentration may vary from 3% w/w to 20% w/w.

Advantageously, the one skilled in the art may use a Dextran composition selected in a group comprising those which are marketed under the brand names of Hemodex®, Macrodex®, Rheomacrodex®, as well as Plasmacair®.

Illustratively, the dextran composition marketed under the brand name of Macrodex® comprises 6% w/w of Dextran 70 and has an oncotic pressure of 56-68 mm Hg (Miltra et al., 2009, Indian J Anaesth, Vol. 53 (n° 5): 592-607).

In embodiments wherein the macromolecule of interest is a hydroxyethyl starch (HES), the HES concentration ranges from 1% w/w to 15% w/w, such as from 3% w/w to 10% w/w.

In embodiments wherein the macromolecule of interest is a hydroxyethyl starch (HES), it may be used a composition selected in a group comprising those marketed under the brand names of Voluven®, Restorvol®, Lomol®, Heafusine®, Heloes® and Hesteril®.

Illustratively, the HES composition marketed under the brand name of Hextend® comprises 6% w/w of a HES having a molecular weight of 670 kDa, and a molar substitution ratio of 0.75, has an oncotic pressure of 25-30 (Miltra et al., 2009, Indian J Anaesth, Vol. 53 (n° 5): 592-607).

Illustratively, the HES composition marketed under the brand name of Hetastarch® comprises 6% w/w of a HES having a molecular weight of 450 kDa, a molar substitution ratio of 0.7 and a C2/C6 ratio of 5, has an oncotic pressure of 25-30 (Miltra et al., 2009, Indian J Anaesth, Vol. 53 (n° 5): 592-607).

Illustratively, the HES composition marketed under the brand name of Pentastarch® comprises 10% w/w of a HES having a molecular weight of 260 kDa, and a molar substitution ratio of 0.45, has an oncotic pressure of 55-60 (Miltra et al., 2009, Indian J Anaesth, Vol. 53 (n° 5): 592-607).

Illustratively, the HES composition marketed under the brand name of Elohes® comprises 6% w/w of a HES having a molecular weight of 200 kDa, a molar substitution ratio of 0.62 and a C2/C6 ratio of 10, has an oncotic pressure of 25-30 (Miltra et al., 2009, Indian J Anaesth, Vol. 53 (n° 5): 592-607).

Illustratively, the HES composition marketed under the brand name of Hesteril® comprises 6% w/w of a HES having a molecular weight of 200 kDa, a molar substitution ratio of 0.5 and a C2/C6 ratio of 5-6, has an oncotic pressure of 30-37 (Miltra et al., 2009, Indian J Anaesth, Vol. 53 (n° 5): 592-607).

Illustratively, the HES composition marketed under the brand name of Lomol® comprises 10% w/w of a HES having a molecular weight of 200 kDa, a molar substitution ratio of 0.5 and a C2/C6 ratio of 6, has an oncotic pressure of 59-82 (Miltra et al., 2009, Indian J Anaesth, Vol. 53 (n° 5): 592-607).

Illustratively, the HES composition marketed under the brand name of Tetrasearch® comprises 6% w/w of a HES having a molecular weight of 130 kDa, a molar substitution ratio of 0.4 and a C2/C6 ratio of 9, has an oncotic pressure of 36 (Miltra et al., 2009, Indian J Anaesth, Vol. 53 (n° 5): 592-607).

Illustratively, the HES composition marketed under the brand name of Heafusine® comprises 6% w/w of a HES having a molecular weight of 200 kDa, a molar substitution ratio of 0.5 and a C2/C6 ratio of 5-6.

Illustratively, the HES composition marketed under the brand name of Restorvol® comprises 6% w/w of a HES having a molecular weight of 130 kDa, a molar substitution ratio of 0.4 and a C2/C6 ratio of 6.

Illustratively, the HES composition marketed under the brand name of Voluven® comprises 6% w/w of a HES having a molecular weight of 130 kDa, a molar substitution ratio of 0.4 and a C2/C6 ratio of 9.

Illustratively, the HES composition marketed under the brand name of Isovol® comprises 6% w/w of a HES having a molecular weight of 130 kDa, a molar substitution ratio of 0.4 and a C2/C6 ratio of 9.

In embodiments wherein the macromolecule of interest is a gelatin, it may be used a liquid solution comprising a gelatin concentration ranging from 2% w/w to 10% w/w.

Advantageously, the one skilled in the art may use a gelatin composition selected in a group comprising those which are marketed under the brand names of Gelofusine®, Plasmion®, Plasmagel®, Geloplasma®, Hextend®, Hetastarch®, Pentastarch®, Voluven®, as well as Haemaccel®.

Illustratively, the fluid gelatin composition marketed under the brand name of Geloplasma® comprises 3% w/w gelatin and has an oncotic pressure of 26-29 (Miltra et al., 2009, Indian J Anaesth, Vol. 53 (n° 5): 592-607).

Illustratively, the urea-linked gelatin marketed under the brand name of Haemaccel® comprises 3.5% w/w gelatin and has an oncotic pressure of 25-29 (Miltra et al., 2009, Indian J Anaesth, Vol. 53 (n° 5): 592-607).

Illustratively, the gelatin marketed under the brand name of Plasmion® comprises 3.0% w/gelatin.

In preferred embodiments of a pharmaceutical composition for used according to the invention, the said composition in its ready-to-use form has a relatively low osmolarity, and has preferably an osmolarity of about 300 mosmoles/kg, such as an osmolarity ranging from 290 mOsm/kg to 300 mOsm/kg.

The invention also relates to treatment of macular edema wherein administration of an oncotic-pressure increasing macromolecule may be combined with an administration of one or more other active agents, so as to further increase the anti-edema effect of the said treatment.

In some embodiments, the said one or more other active agents may be selected in a group comprising anti-inflammatory agents, which include corticosteroids.

Corticosteroids may be selected in the group of glucocorticoids such as dexamethasone, fluocinolone acetonide, methylprednisolone, betamethasone, mineralocorticoids receptor antagonists such as spironolactone or eplerenone or any molecule that neutralizes mineralocorticoid receptors such as sirNAs.

The present invention is further illustrated by, without in any way being limited to, the examples herein.

EXAMPLES

Example 1

Retinal Gene Upregulation Upon Increasing Vitreous Oncotic Pressure 1.1. Retinal Gene Upregulation Upon Anti-VEGF Antibody Injection in the Vitreous A volume of 5 µl of several preparations have been injected in the vitreous of Lewis Albinos rat (8-12 weeks) and their transcriptomic effects on the retina and the RPE/choroid at 24 hrs have been evaluated:

Preparations Tested

Lucentis® (Ranibizumab: 0.1 mg/mL)

"Fab+Polysorbate": Human isotypic Fab (OAMA04119, Aviva Systems Biology)+polysorbate 20: (Fab+Poly, 0.1 mg/ml+0.01%) which is the polysorbate 20 concentration in the Lucentis preparation Control solution: $H_2O$ Importantly, Avastin® (bevacizumab) and Lucentis® (ranibizumab) do not neutralize rat VEGF.

Twelve eyes per condition have been tested and the RNA has been extracted for RNA sequencing.

The results of RNA sequencing showed that 89% of the genes differentially regulated between control and Lucentis® preparation are common to the genes regulated by the Fab+polysobate preparation, which results demonstrate that a solution containing a non-active Fab exerts similar transcriptomic effects than Lucentis®.

The results of RNA sequencing showed that (i) 139 genes are regulated by Lucentis® preparation versus Control preparation, and also showed that (ii) 88% of those genes are common to those regulated by Fab+Poly versus Control.

Analysis of GO Terms

GO terms were analyzed on the 122 common genes, (i) 94 GO terms (44%) belong to inflammation/immunity-related genes, (ii) 16 (8%) GO terms belong to in cell death-related genes, (iii) 10 GO terms (4.6%) belong to Hydro-ionic regulations-related genes and (iv) 3 GO terms belong to genes related to angiogenesis response and hypoxia response (including Serpine1, Angptl4 et Tnfrsfl).

Analysis of KEGG Pathways

The results showed that the differentially regulated genes belong to 15 enriched pathways, including (i) 13 pathways relating to inflammation/Immunity and (ii) 1 pathway relating to cell adhesion These results led to the hypothesis that Lucentis drug (Ranibizumab) exerts «off target» effects that are related to the nature of the molecule (protein) and not to the neutralization of VEGF only.

1.2. Retinal Gene Upregulation Upon Injection of Unrelated Antibodies in the Vitreous A similar experiment as that described in paragraph 1.1. above was performed by using an intravitreal injection of (i) 5 µl of Avastin® (Bevacizumab: 0.25 mg/ml) or of (ii) 5 µl of an isotypic human IgG (ABIN619681, available from Antibodies-Online®)+Polysorbate 20 (IgG+Polysorbate, 0.25 mg/ml+0.04%) which is the polysorbate concentration contained in the Avastin® formulation.

The results from the resulting RNA sequencing showed that 60 genes are common to both treatments (i) and (ii) above. The more regulated genes are listed below, they are all up-regulated except Agt (angiotensinogene).

These upregulated genes are the following: A2m, Agt, Arpc1b, C1R, C1S, C3, Cd14, Cebpd, Ch/3/1, Clic1, Clu, Coro1a, Cp, Crym, Cts2, Gfap, Jak3, Krt15, Lcn2, Litaf, Lrg1, Mt1a, Mt1h12, Mt1X, Nudt6, Pdpn, Prss56, Pycard, Rrm2, Sbno2, Serpina3, Serping1, Slc14a1, Socs3, Spp1, Tagin2 andTimp1.

1.3. Retinal Gene Upregulation Upon Increasing the Vitreous Oncotic Pressure by Intravitreous Injection of an Oncotic Pressure-Increasing Macromolecule The transcriptomic effect of Plasmion® 3%® (320 mmol/l, which is conventionally used as a vascular expansion composition of 1 for 3 hrs after intravenous injection).

Composition of Plasmion® (Fluidic Modified Gelatin):

| | |
|---|---|
| Amount expressed as anhydrous gelatin | 3.0000 g |
| Sodium chloride | 0.5382 g |
| Hexahydrated magnesium chloride | 0.0305 g |
| Protassium chloride | 0.0373 g |
| Sodium (S)-lactate solution | 0.3360 g |

Pour 100 ml de solution pour perfusion.

A volume of 5 µl of Plasmion® solution was injected in each tested eye.

The expression level of various genes has been tested by using the RT-PCR method on n=12 eyes. The effect of injection of Plasmion® was compared to the effect of sham injection (needle without any volume injected).

Figure 2:
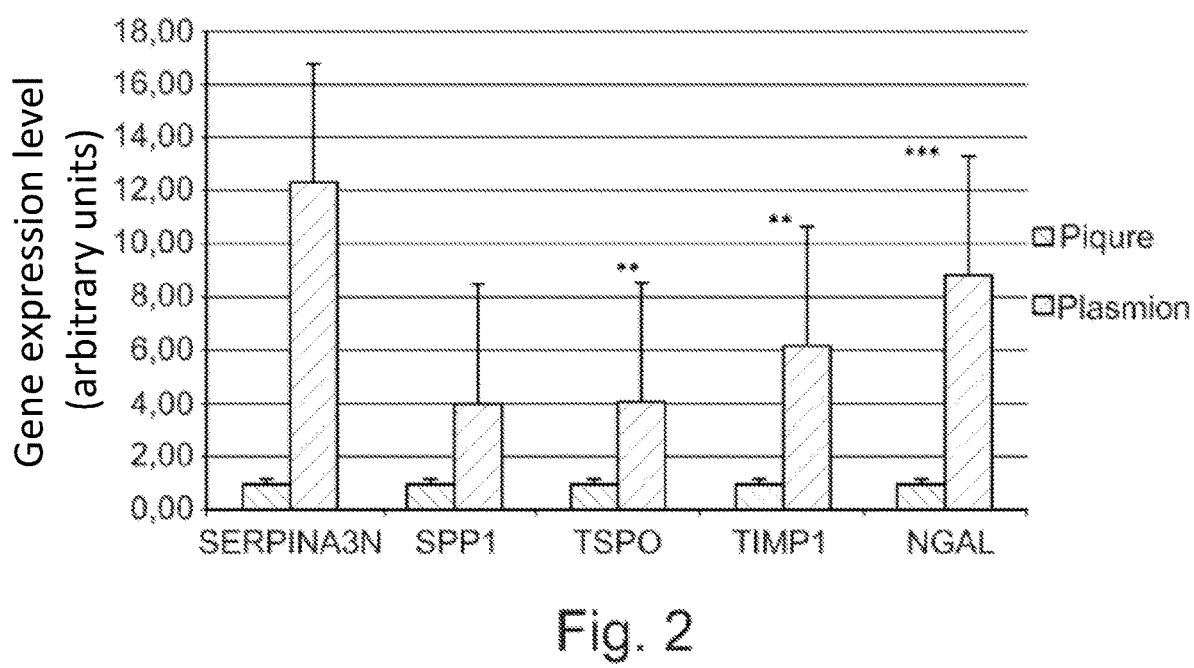
FIG. 2 illustrates the gene expression level of selected genes in the retina upon increasing vitreous oncotic pressure with a 3% w/w gelatin composition (Plasmion®). Ordinates: gene expression level, as expressed in arbitrary units. Abscissa: each group of two bars depicts the expression level of a specific selected gene with (i) left bar for control experiment and (ii) right bar for intravitreous injection of Plasmion®. Group of two bars, from the left to the right of FIG. 2 represent the following selected genes: SERPINA3N, SPP1, TSPO, TIMP1 and NGAL.

The results are shown in FIGS. 1 and 2. The results showed that various genes were upregalulated, which include the following genes: (i) Pdpn, Crym, Agt, Slc14a1, Slc39a1, Pycard, Tnf-R1, Galectin3bp and Clic1 (see in FIG. 1) and (ii) Serpina3n, Spp1, Tspo, Timp1 and Ngal (see in FIG. 2).

Example 2

Treatment of Macular Edema by Intravitreous Injection of an Oncotic Pressure-Increasing Macromolecule In order to demonstrate that anti-edematous effects on the neuroretina could be achieved similarly by the Plasmion® composition, the above-described composition of Fab+Polysorbate and the Lucentis® composition, rat retinal explants have been incubated in hypo-osmotic conditions in order to create edema and the protective effects of each of these compositions have subsequently been tested.

A. Materials and Methods

Rat retinal explants were first incubated with hypo osmotic solution for 4 minutes to induce retinal edema. Then, these rat retinal explants were incubated for 1 hour with either extracellular (EC) solution or with EC+Lucentis®, Fab+polysorbate, or Plasmion® at the concentrations below:

Extracellular solution (EC) 500 ml adjusted to pH 7.4 with TRIS 1M (6.05 g in 50 ml)

|  | Concentration (mM) |
| --- | --- |
| NaCl | 136 |
| KCl | 3 |
| CaCl2 | 2 |
| MgCl2 | 1 |
| Hepes | 10 |
| Glucose | 11 |

Hypo osmotic solution: EC+40% $H_2O_2$

Solution EC+Baryum chloride: (1 mM, MM=224.26) 1.12 mg dans 5 ml ou 2.24 mg dans 10 ml.

Solution Lucentis® at 0.1 mg/ml

Solution Fab+Poly at 0.1 mg/ml

Solution Plasmion® 0.1%

The experiment was repeated three times (n=2 explants/conditions X3).

At the end of the experiments, the rat explants were included for cryosection without fixation and then stained with DAPI for nucleus staining and with GFAP for glial cells staining. Retinal thickness was measured on at least 10 sections per retina from the inner layer to the outer nuclear layer border.

B. Results

Figure 3:
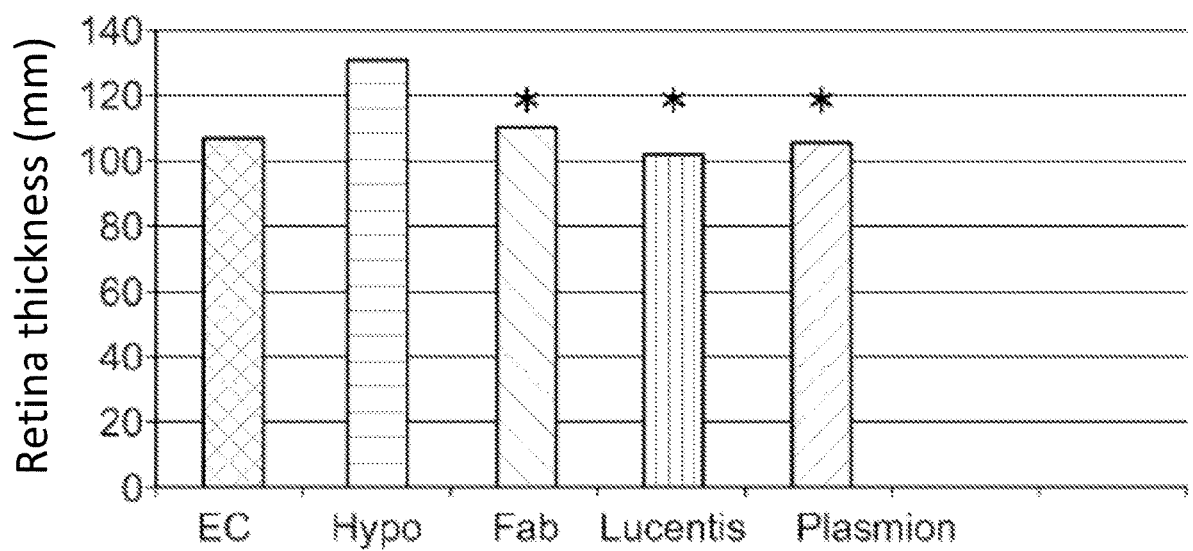
FIG. 3 illustrates the effect of increasing the oncotic pressure of the retina outer environment on macular edema. Ordinate: retina thickness as expressed in millimeters. Abscissa, from the left to the right of FIG. 3: (i) extracellular medium solution (EC), (ii) hypo-osmotic solution (Hypo), (iii) purified human IgG Fab fragment (OAMA04119 from Aviva Systems Biology), (iv) ranibizumab (anti-VEGF Fab fragment) from Lucentis®, (v) 3% w/w gelatin composition (Plasmion®).

The results are depicted in FIG. 3.

Incubation in hyposomotic solution induced a significant increase in retinal thickness (from 107.7±2.4 μm to 131.7±20.7 μm, p<0.05). Treatment with Fab, lucentis or plasmion induced a significant reduction in thickness (110.6±3, 102.6±21, 105±2.4 μm, p<0.05).

CONCLUSION

Plasmion®, Fab composition and Lucentis® exert similar anti-edematous effects on hypo-osmotic-induced retinal edema.

These results show that macular edema may be efficiently treated by using an oncotic pressure-increasing macromolecule

The invention claimed is:

1. A method of treating macular edema in an individual in need thereof, comprising administering to the individual by intravitreous injection, an oncotic pressure-increasing macromolecule having a molecular weight of 25 kDa or more and which does not recognize VEGF, as the sole active ingredient, wherein the oncotic pressure-increasing macromolecule is a protein macromolecule consisting of gelatin.

2. The method according to claim 1, wherein the protein macromolecule is gelatin in a 2%-10% w/w gelatin composition.

3. The method according to claim 1, wherein the oncotic pressure-increasing macromolecule is in a composition adapted for dosage units having a volume ranging from 10 μl to 500 μl.

4. A method of treating a macular edema disorder in an individual in need thereof, comprising administering to the individual by intravitreous injection, an oncotic pressure-increasing macromolecule having 25 kDa or more and which does not recognize VEGF, as the sole active ingredient, wherein the oncotic pressure-increasing macromolecule is a protein macromolecule consisting of gelatin, and wherein the macular edema disorder is selected from the group consisting of age-related macular degeneration, diabetic retinopathy, uveitis, retinal vein occlusion, retinitis pigmentosa and pseudophakic macular edema.

* * * * *